(12) United States Patent
Geistlich et al.

(10) Patent No.: US 6,221,109 B1
(45) Date of Patent: Apr. 24, 2001

(54) METHOD OF PROTECTING SPINAL AREA

(75) Inventors: Peter Geistlich, Stansstad (CH); Philip J. Boyne, Loma Linda, CA (US); Lothar Schlösser, Darmstadt (DE)

(73) Assignee: Ed. Geistlich Söhne AG fur Chemische Industrie (CH)

( * ) Notice: Subject to any disclaimer, the term of this patent is extended or adjusted under 35 U.S.C. 154(b) by 0 days.

(21) Appl. No.: 09/396,418

(22) Filed: Sep. 15, 1999

(51) Int. Cl.⁷ .................................................... A61F 2/44
(52) U.S. Cl. ...................................... 623/17.11; 623/23.74
(58) Field of Search .............................. 623/17.11, 16.11, 623/17.12, 17.16, 23.64, 23.71, 23.72, 23.74; 606/152

(56) References Cited

U.S. PATENT DOCUMENTS

| | | | |
|---|---|---|---|
| 4,013,078 | * 3/1977 | Feild | 606/1 |
| 4,863,668 | * 9/1989 | Griffiths et al. | 606/152 |
| 4,870,966 | * 10/1989 | Dellon et al. | 606/152 |
| 4,877,029 | * 10/1989 | Valentini et al. | 606/152 |
| 5,611,354 | * 3/1997 | Alleyne | 606/69 |
| 5,830,493 | * 11/1998 | Yokota et al. | 623/23.61 |
| 5,837,278 | 11/1998 | Geistlich et al. | |

FOREIGN PATENT DOCUMENTS 9625961    8/1996   (WO).

* cited by examiner

Primary Examiner—Michael J. Milano
Assistant Examiner—Brian Pellegrino
(74) Attorney, Agent, or Firm—Rothwell, Figg, Ernst & Manbeck

(57) ABSTRACT

A method of protecting a spinal area of a patient includes the step of positioning a sheet of collagen membrane material so as to surround at least a portion of a patient's spinal chord. The sheet of collagen membrane preferably includes at least one barrier layer with a smooth face to inhibit cell adhesion and act as a barrier to prevent passage of cells therethrough. When surgery involves placement of s vertebrae replacement material between vertebrae, the collagen membrane material can be positioned so as to surround at least a portion of the vertebrae replacement material.

16 Claims, 2 Drawing Sheets

METHOD OF PROTECTING SPINAL AREA

BACKGROUND OF THE INVENTION

1. Field of the Invention

The present invention relates to the field of protecting a spinal area of a patient during or after surgery.

2. Description of the Background Art

There are numerous spinal surgeries performed each year to treat disc injuries, repair, remove or fuse vertebrae, or combinations thereof. During such surgeries, it is desirable to protect the spinal cord and the dura sheath surrounding the spinal cord from injury. Spinal surgeries often also involve insert of bone graft material to repair or replace damaged vertebrae. During the subsequent healing process, it is desirable to protect the spinal area from ingrowth of connective tissue and undesired cells which might interfere with proper healing.

There remains a need in the art for new methods of protecting spinal areas of a patient during and after surgery.

SUMMARY OF THE INVENTION

In accordance with the present invention, a method of protecting a spinal area of a patient comprises positioning a sheet of collagen membrane material so as to surround at least a portion of a patient's spinal chord.

DETAILED DESCRIPTION OF THE INVENTION

The present invention provides a method of protecting areas of the spinal chord and column during and after spinal surgery.

Figure 1:
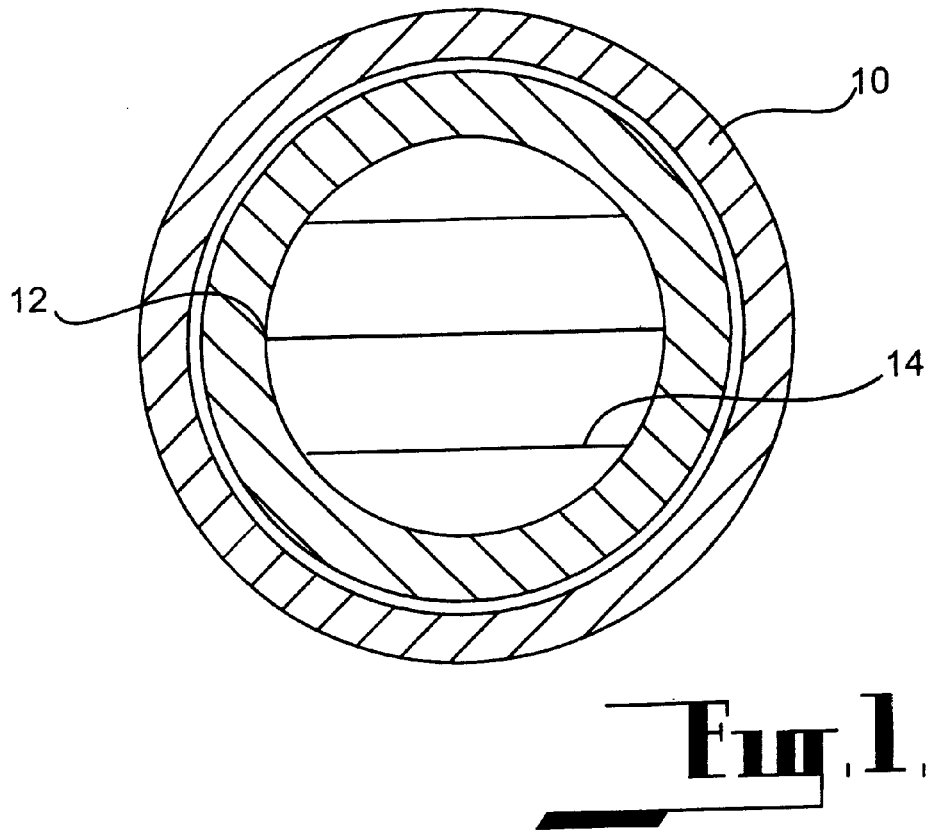
FIG. 1 is a sectional schematic view showing a spinal chord surrounded by a sheet of collagen membrane material in accordance with one embodiment of the present invention.

In accordance with one embodiment, during spinal surgery in which the dura sheath surrounding the spinal chord is exposed, a sheet of collagen membrane material 10 is positioned adjacent the dura sheath 12 surrounding a patient's spinal chord 14 so as to protect the dura sheath 12. See FIGS. 1 and 2.

In accordance with one embodiment, the collagen membrane material is comprised of at least one barrier layer having at least one smooth face 16 so as to inhibit cell adhesion thereon and act as a barrier to prevent passage of cells therethrough. See FIG. 3. In accordance with this embodiment, the barrier layer further has a fibrous face 18 opposite the smooth face 16, the fibrous face allowing cell growth thereon. In preferred embodiments, the barrier layer is predominantly collagen I, collagen III or a mixture thereof. One suitable material is Biogide®, from Ed. Geistlich Söhne AG für Chemische Industrie, the assignee of the present invention. The Biogide® material is described in U.S. Pat. No. 5,837,278, incorporated herein by reference.

Figure 3:
FIG. 3 is a side elevation schematic view showing a single-layered membrane for use in accordance with the present invention.
Figure 4:
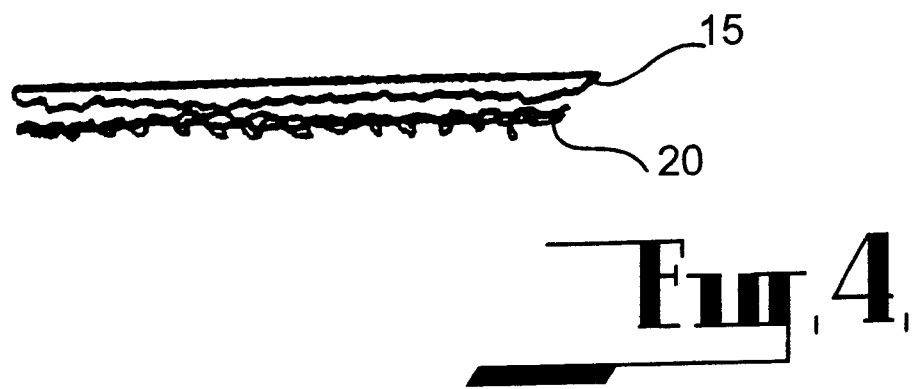
FIG. 4 is a side elevation schematic view showing a double-layer membrane for use in accordance with the present invention.

FIG. 4 shows a second type of membrane which may be used in accordance with the present invention. This membrane includes a barrier layer 15 as shown in FIG. 3, and further includes a matrix layer 20 predominantly of collagen II having an open sponge-like texture. A collagen membrane as shown in FIG. 4 is described in PCT application no. PCT/GB 98/02976 designating the U.S. and claiming priority from U.K. patent application no. 9721585.9, filed Oct. 10, 1997, incorporated herein by reference.

In one preferred embodiment, a collagen membrane material as shown in FIG. 4 is utilized, wherein the barrier layer 15, the matrix layer 20, or both are impregnated with a glycosaminoglycan. Examples of suitable glycosaminoglycans include hyaluronic acid, chondroitin 6-sulphate, keratin sulphate or dermatan sulphate.

Figure 5:
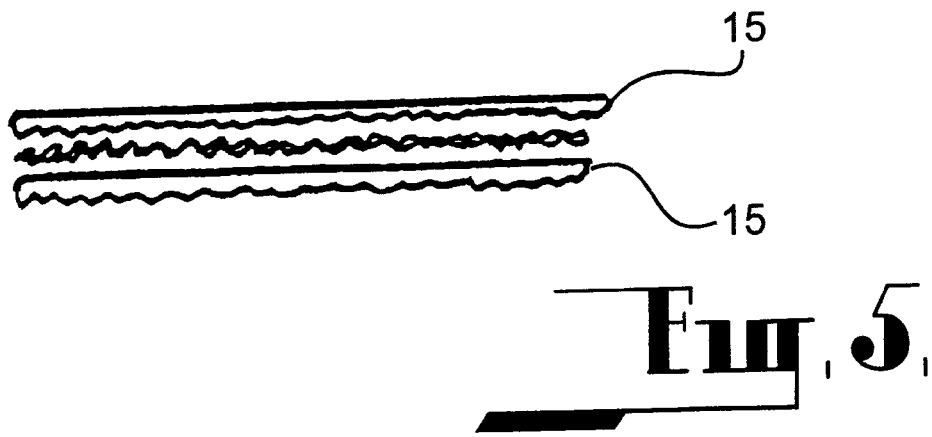
FIG. 5 is a side elevation schematic view showing a triple-layer membrane for use in accordance with the present invention.

FIG. 5 shows still another type of membrane suitable for use in accordance with the present invention. The membrane of FIG. 5 includes two barrier layers 15, between which is sandwiched a resorbable polymer layer. In preferred embodiments, the polymer is a polylactic acid polymer. Examples of membranes as shown in FIG. 5 are described in U.K. patent application no. 990611.8, filed Mar. 23, 1999, WP file number 69092.

Referring back to FIG. 2, in accordance with another embodiment of the present invention, a sheet 10' of collagen membrane material is positioned so as to surround at least a portion of a vertebrae 22 surrounding the spinal chord 14. In certain surgeries, a vertebrae implant material 24 such as resorbable bone mineral may be positioned between two vertebrae 22a and 22b so as to facilitate fusion of vertebrae 22a and 22b. In accordance with this aspect, the invention encompasses a sheet of collagen material 10' so as to surround at least a portion of the vertebrae implant material 24. One suitable vertebrae implant material is Bio-Oss® from Ed. Geistlich Söhne AG Für Chemische Industrie, the assignee of the present invention. Bio-Oss® is described in U.S. Pat. Nos. 5,167,961 and 5,417,975 incorporated herein by reference. Another suitable vertebrae implant material is Bio-Oss Collagen® from Ed. Geistlich Söhne AG Für Chemische Industrie, which is resorbable bone mineral in a collagen matrix. Bio-Oss Collagen® is described in U.S. Pat. No. 5,573,771 incorporated herein by reference. The present invention also is applicable to other bone graft methods, such as the "cage technique", in which a net of titanium enclosing bone graft material is inserted between vertebrae. In accordance with these embodiments, the sheet of collagen membrane material protects the implant material against ingrowth of connective tissue and other cells from outside adjacent bone material, which might interfere with osteocytes and other bone-regenerating cells from fully incorporating the spinal implant material into the spinal column for maximum strength and healing.

Figure 2:
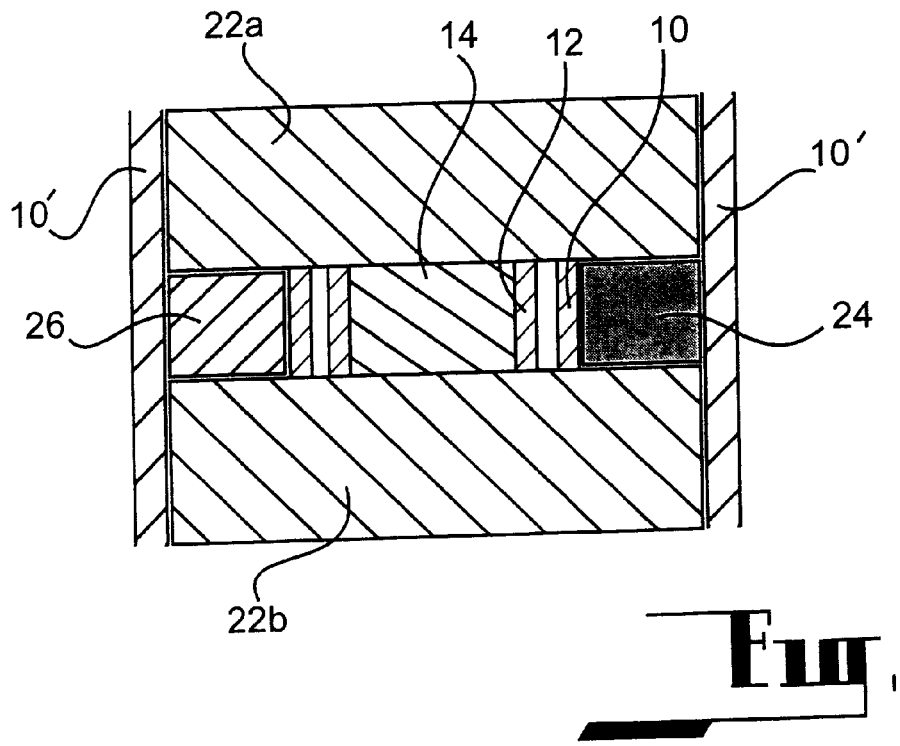
FIG. 2 is a schematic plan view in partial cross-section showing a second embodiment of the present invention wherein a first sheet of collagen membrane material is immediately adjacent a patient's spinal chord, and a second sheet of collagen membrane material is positioned outside a patient's vertebrae, spinal disc and inserted vertebrae implant material.

The method of the present invention also encompasses positioning a sheet of collagen membrane material 10' so as to surround at least a portion of a spinal disc 26 surrounding spinal chord 14 as shown in FIG. 2. In the embodiment shown in FIG. 2, the dura 12 has been surrounded by a collagen membrane 10 in accordance with the present invention, and in addition thereto, a second collagen membrane 10' has been wrapped around vertebrae 22a and 22b, as well as disc 26 and vertebrae implant material 24 for protection thereof. The present invention is thus capable of protecting the spinal chord dura from physical injury during surgery, and the barrier layer of membrane 10' protects the surgical site from ingrowth of unwanted cells during the healing process when membrane 10' is wrapped around the spinal column as shown in FIG. 2. The collagen membrane material 10, 10' is gradually resorbed into the patient's body, avoiding any necessity of having to surgically remove the membranes after healing.

While the invention has been described in detail, it is not intended that the description and accompanying drawings be interpreted in a limiting sense.

What is claimed is:

1. A method of protecting a spinal area of a patient comprising positioning a sheet of resorbable collagen membrane material so as to substantially wrap the collagen membrane material around a patient's spinal chord wherein said collagen membrane material is comprised of at least one barrier layer having at least one smooth face so as to inhibit cell adhesion thereon and act as a barrier to prevent passage of cells therethrough.

2. The method of claim 1 wherein said barrier layer further has a fibrous face opposite said smooth face, said fibrous face allowing cell growth thereon.

3. The method of claim 2 wherein said barrier layer is predominantly collagen I, collagen III or a mixture thereof.

4. The method of claim 3 wherein said collagen membrane further comprises a matrix layer predominantly of collagen II having an open sponge-like texture.

5. The method of claim 4 wherein said barrier layer, said matrix layer or both, are impregnated with glycosaminoglycan.

6. The method of claim 5 wherein the glycosaminoglycan is hyaluronic acid, chondroitin 6-sulphate, keratin sulphate or dermatan sulphate.

7. The method of claim 2 wherein said membrane material further comprises a second barrier layer, and a resorbable polymer layer sandwiched between the barrier layers.

8. The method of claim 7 wherein said polymer is a polylactic acid polymer.

9. The method of claim 1 wherein said sheet is positioned adjacent a dura sheath of said spinal chord, so as to protect said dura sheath.

10. A method of protecting a spinal area of a patient comprising positioning a sheet of resorbable collagen membrane material so as to substantially wrap the collagen membrane material around a patient's spinal chord, wherein said sheet is positioned adjacent a dura sheath of said spinal chord, so as to protect said dura sheath, further comprising the step of inserting a vertebrae implant material outside said sheet adjacent said dura sheath, and further positioning a second sheet of collagen membrane material around at least a portion of said vertebrae implant material.

11. The method of claim 10 wherein said second sheet of collagen membrane material also surrounds at least a portion of a vertebrae surrounding said spinal chord.

12. A method of protecting a spinal area of a patient in which a vertebrae implant material has been positioned adjacent to the patient's spinal chord in an intervertebral space between two vertebrae, comprising positioning a sheet of resorbable collagen material adjacent the intervertebral space so as to substantially wrap the collagen membrane material around the vertebrae implant material.

13. The method of claim 12 wherein said sheet of collagen membrane material includes at least one barrier layer having a smooth face that protects against ingrowth of connective tissue into said vertebrae implant material.

14. The method of claim 12 wherein said sheet of collagen membrane material is positioned to also surround at least a portion of a vertebrae surrounding said spinal chord.

15. The method of claim 1 wherein said sheet is positioned so as to surround at least a portion of a vertebrae surrounding said spinal chord.

16. The method of claim 1 wherein said sheet is positioned so as to surround at least a portion of a spinal disc surrounding said spinal chord.

* * * * *